(12) United States Patent
Cawse

(10) Patent No.: US 8,461,275 B2
(45) Date of Patent: Jun. 11, 2013

(54) CURING AGENTS AND PROCESS FOR THEIR MANUFACTURE

(75) Inventor: John Cawse, Dublin, CA (US)

(73) Assignee: Hexcal Composites Limited, Duxford (GB)

( * ) Notice: Subject to any disclaimer, the term of this patent is extended or adjusted under 35 U.S.C. 154(b) by 336 days.

(21) Appl. No.: 13/055,142

(22) PCT Filed: Aug. 3, 2009

(86) PCT No.: PCT/GB2009/050969
§ 371 (c)(1),
(2), (4) Date: Jan. 21, 2011

(87) PCT Pub. No.: WO2010/018392
PCT Pub. Date: Feb. 18, 2010

(65) Prior Publication Data
US 2011/0130525 A1    Jun. 2, 2011

(30) Foreign Application Priority Data
Aug. 13, 2008 (GB) .................................. 0814765.4

(51) Int. Cl.
| C07C 211/55 | (2006.01) |
| C08L 63/00 | (2006.01) |
| C08L 63/02 | (2006.01) |
| C08L 63/04 | (2006.01) |

(52) U.S. Cl.
USPC ........... 525/523; 525/396; 525/407; 525/423; 525/438; 525/454; 525/463; 525/471; 525/504; 564/321

(58) Field of Classification Search
None
See application file for complete search history.

(56) References Cited

U.S. PATENT DOCUMENTS

| 3,674,749 A | 7/1972 | Craven |
| 3,907,752 A | 9/1975 | Frost |
| 4,167,489 A * | 9/1979 | Osman ...................... 252/299.64 |
| 4,168,364 A | 9/1979 | Seltzer et al. |
| 4,208,343 A | 6/1980 | Frost |

FOREIGN PATENT DOCUMENTS

| EP | 0327125 A2 | 8/1989 |
| FR | 2476068 | 8/1981 |
| GB | 1369823 | 10/1974 |
| SU | 462817 | 3/1975 |
| SU | 755809 | 8/1980 |
| SU | 1219593 | 7/1984 |

OTHER PUBLICATIONS

Ponomarev, et al, "Reaction of phthalodinitrile with aromatic o-cyanamines", Russian Chemical Bulletin, vol. 29, No. 8, Aug. 1, 1980.

Chenskaya et al., Journal of Molecular Structure, 1996, 381, pp. 149-156.

* cited by examiner

*Primary Examiner* — Robert Sellers
(74) *Attorney, Agent, or Firm* — W. Mark Bielawski; David J. Oldenkamp

(57) ABSTRACT

Compounds having the formula (I) wherein L is a linking group, at least one of $R_1$ to $R_{10}$ comprises the group C≡N, at least one of $R_1$ to $R_5$ and at least one of $R_6$ to $R_{10}$ comprise the group $NH_2$ for use as curing agents in an epoxy resin, together with a process for their synthesis and composites comprising the curing agents.

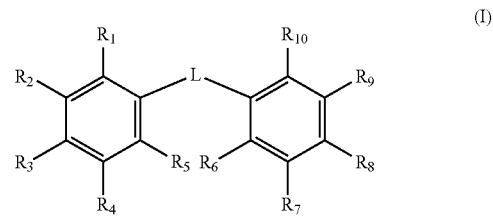

14 Claims, No Drawings

CURING AGENTS AND PROCESS FOR THEIR MANUFACTURE

FIELD OF THE INVENTION

The invention relates to curable epoxy resins comprising a curing agent, a novel process for the synthesis of the curing agents, and composite materials comprising the cured resins.

BACKGROUND

Curing agents, or hardeners, are used to react with a monomer, such as epoxy, isocyanate, acid anhydride etc, to produce a hardened polymeric resin.

The resulting resins are employed in a wide range of industries and in a wide range of applications. The chemical and physical properties of the resulting resins vary widely, primarily depending on the choice of monomer and of the curing agent.

There is an ongoing demand for resins having improved physical and chemical properties, particularly for use in demanding applications, such as for use in aerospace composite materials. Of particular interest are resins which have a high modulus and with less tendency to absorb water. A resin with increased modulus provides improved compression, flexure and tensile properties in composite materials in which they are employed.

It would therefore be highly desirable to develop new curing agents which can produce resins having increased modulus and less tendency to absorb water.

SUMMARY OF INVENTION

The invention relates to a curable epoxy resin comprising a compound having the formula

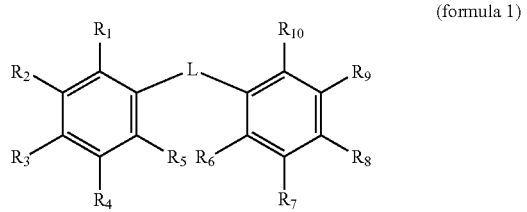

(formula 1)

wherein L is a linking group, at least one of $R_1$ to $R_{10}$ comprises the group C≡N, at least one of $R_1$ to $R_5$, and at least one of $R_6$ to $R_{10}$ comprises the group $NH_2$.

Such compounds have been found to make very effective curing agents, and when used as curing agents along with suitable monomers, produce materials such as epoxy, said materials having an increased modulus and less tendency to absorb water.

In a further aspect, the invention relates to a cured composite material comprising an epoxy resin cured with a curing agent according to formula 1.

L can be any suitable linking group but is preferably selected from $CH_2$, $SO_2$, O and $CHCH_3$. Preferably L is $CH_2$.

Preferably the compound has at least two C≡N groups, preferably at least one on each benzene ring, i.e. at least one of $R_1$ to $R_5$ comprises a C≡N group and at least one of $R_6$ to $R_{10}$ has a C≡N group. In a preferred embodiment, one of $R_1$ to $R_5$ comprises a C≡N group and one of $R_6$ to $R_{10}$ has a C≡N group.

In a preferred embodiment the compounds are symmetrical, i.e. $R_1=R_{10}$, $R_2=R_9$, $R_3=R_8$, $R_4=R_9$ and $R_5=R_6$.

Preferably each of $R_1$ to $R_{10}$ comprise from H or $C_1$ to $C_5$ alkyl irrespective of whether or not a C≡N or $NH_2$ group is also present. Preferably each of $R_1$ to $R_{10}$ comprise H or $C_1$ to $C_4$ alkyl, more preferably H or $C_1$ to $C_3$ alkyl.

It is further preferred that on any one benzene ring any C≡N group and $NH_2$ group are not attached to carbons adjacent to each other in the ring.

The compounds can be usefully employed in resins, adhesives, both rigid and flexible foams, elastomers, fibres and composites. They can be used as sole curatives or in admixture with other known amines and other curing agents. They can be used with or without the usual curing accelerators and/or catalysts. A preferred curing agent to form a mixture with is a diaminodiphenylsulphone.

Examples of preferred curing agents that may be used in combination with the compounds of the present invention include: 4,4'-diamino-diphenylmethane; 4,4'-diaminodiphenyl sulphone (4,4'-DDS); 3,3'-diaminodiphenyl sulphone (3,3'-DDS); dicyandiamide; m-phenylene diamine; p-phenylenediamine; methylenebis(2,5-diethylaniline); methylenebis(2-methyl-5-isopropylaniline); methylenebis(3-chloro-2,5-diethylaniline); 4,4'-methylenebis(2-ethylaniline); 9,9-bis(3-chloro-4-aminophenyl)fluorene; 9,9-bis(4-aminophenyl)fluorene; 9,9-bis(3-methyl-4-aminophenyl)fluorene and others well known in the art.

Examples of epoxy resins that may be included are: the glycidyl derivatives of bisphenol A and bisphenol F and of higher molecular weight adducts thereof, the glycidyl derivatives of p-aminophenol and m-aminophenol; diglycidyl aniline; polyglycidyl derivatives of polyhydroxy compounds such as glycerol, trimethylolpropane and butanediol; 3,4-epoxycyclohexylmethyl 3,4-epoxycyclohexanecarboxylate; vinylcyclohexene dioxide; hydrogenated bisphenol A diglycidyl ether; bis(2,3-epoxycyclopentyl)ether; the diglycidyl ester of 1,2-cyclohexanedicarboxylic acid; diglycidyl phthalate; the triglycidyl ether of tris(hydroxyphenyl)methane; the diglycidyl ether of bis(4-hydroxyphenyl)fluorene; the diglycidyl ether of brominated bisphenol A; the glycidyl derivative of the adduct formed from dicyclopentadiene and phenol; the glycidyl derivatives of methylene bis-(2,7-dihydroxynaphthalene); the glycidyl derivatives of methylene bis-(2-hydroxynaphthalene); glycidyl ethers from phenol novolaks and cresol novolaks; the tetraglycidyl amine of methylenebisaniline, the tetraglycidyl derivative of m-xylylene diamine; and other epoxy resins well known in the art, including liquid, solid or semi-solid examples.

Toughening agents may also optionally be present in the formulation including polyamides, polycarbonates, polyacetal, polyphenylene oxide, polyphenylene sulphide, polyarylates, polyethers, polyesters, polyimides, polyamidoimides, polyether imides, polysulphones, polyurethanes, polyether sulphones, polyether ethersulfones and polyether ketones. The toughening agents may be dissolved, partially dissolved, or undissolved in the matrix resin.

Examples of compounds according to the invention are shown below:

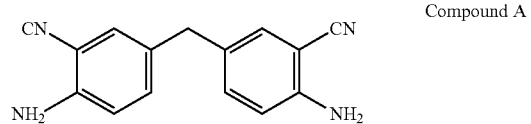

Compound A

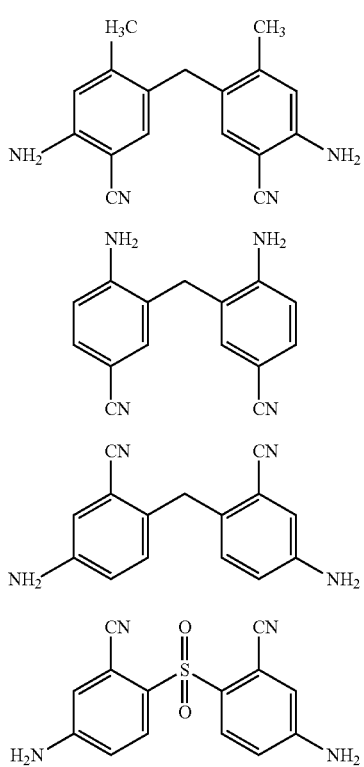

Compound B

Compound C

Compound D

Compound E

One reason why it is believed that these compounds have not been previously considered is because of the well-known difficulty of synthesising nitrile derivatives, particularly in the presence of an amine group.

For the simpler homologues, for instance the aminobenzonitriles, this is not problematic because such derivatives are normally made by the ammoxidation (oxidative treatment over a catalyst in the presence of oxygen) of the corresponding methyl substituted amine: for example, 2-aminobenzonitrile is thus prepared from O-toluidine in the vapour phase. For higher homologues this is difficult because of the low volatility of the amine and because the starting methyl derivative may not be readily available.

Previously known synthesis routes include the dehydration of a carboxylic amide, itself formed from the corresponding carboxylic acid or ester. The dehydration is conventionally carried out using phosphorus pentoxide or phosphorus oxychloride. However, these are powerful reagents and often lead to significant charring of the reaction products. Additionally, the oxychloride can react with the amine functionality which is not desirable. It should be possible to use basic dehydrating reagents such as sulphur trioxide/triethylamine, but these require inconvenient, complex work-up procedures and generate much waste (see U.S. Pat. No. 5,817,827 "Method for the dehydration of amides to nitriles").

Another known route is the Rosenmund von Braun reaction of the corresponding halogen-substituted derivative with copper cyanide. This preferably requires the prior formation of the corresponding bromo derivative. Once again, the work-up is complicated and, if acids are used to remove the copper residues, can generate toxic cyanide gas. Much waste material is again produced.

The present inventors have developed a synthesis route which avoids the disadvantages of known routes.

Thus, in a further aspect, the invention relates to a process for the preparation of a compound according to formula 1, wherein L is a linking group, at least one of $R_1$ to $R_{10}$ comprises the group C≡N, at least one of $R_1$ to $R_5$ and at least one of $R_6$ to $R_{10}$ comprising the group $NH_2$, comprising the steps of bringing starting material comprising

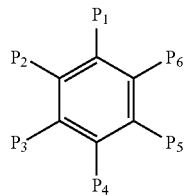

wherein at least one of $P_1$ to $P_6$ comprises C≡N and at least one of $P_1$ to $P_6$ comprises $NH_2$ into intimate contact with a kaolin clay and an aldehyde and reacting to form a compound according to formula 1.

The process is safe, highly selective, provides a high yield at low temperature, and produces little waste. There are no toxic gases evolved during reaction or work up. The catalyst is cheap and can be regenerated. The reaction can be carried out in water or a mixture of water with a mixable solvent.

Preferably the clay is kaolin or kaolinite. A preferred aldehyde is methanal or formaldehyde.

In a preferred embodiment the C≡N group and $NH_2$ group are not attached to carbons adjacent to each other in the ring.

Preferred mixable solvents are alcohols, especially ethanol, methanol and propanol. Other mixable solvents include dimethylformamide, N-methylpyrrolidone, dimethyl sulfoxide and dimethylacetamide. Formaldehyde may be in the form of formalin solution, paraformaldehyde or trioxane or other well known forms of free or combined formaldehyde. The reaction may be conducted at any suitable temperature although if water is used as the reaction medium, the preferred temperature range is from 10° C. to 60° C. For some of the nitrile substituted aromatic amine starting materials, it is preferable to run the reaction at a temperature sufficient to melt the amino nitrile. If the amino nitrile melts at a temperature above about 60° C. it is preferred to use a solvent as mentioned above, or to use a mixture of water and the water mixable solvent in order to solubilise the starting nitrile amine. After the reaction is complete, the required product may be recovered by first filtering off the solid, then adding a solvent for the product and filtering again to remove the kaolin. Suitable solvents for the nitrile amines of the invention are acetone, ethanol, tetrahydrofuran, dimethylformamide and other common solvents. The product may be isolated by crystallisation or precipitation. In some cases, it may not be necessary to remove the clay catalyst from the product and instead the crude product may suffice.

The invention will now be further described, by way of illustration in the following examples.

EXAMPLE 1

Preparation of Compound D 2 g of kaolin (ASP400, Lawrence Industries) was dispersed in 400 ml of distilled water maintained at 45° C. in a 2 litre flask. With continuous stirring, 25 g of 3-aminobenzonitrile was added. The latter melted and formed an emulsion. 10 ml of formaldehyde solution (35%) was added dropwise over 30 minutes to the stirred suspension. Within 10 minutes, a white solid product began to separate. Reaction was continued for a total of 30 minutes after completing the formaldehyde addition. The suspension was filtered and washed with water. The faun coloured residue was extracted into hot tetrahydrofuran and filtered to remove the kaolin. The resulting solution was concentrated on a rotary film evaporator and the solid product was filtered off and washed with industrial methylated spirit. After drying, there was obtained 15.4 g (59% of theoretical yield) of a faun coloured powder, melting point 204-207° C. This was shown by high performance liquid chromatography (HPLC) to be a single compound, compound D.

EXAMPLE 2

In a similar way were prepared:
Compound A, from 2-aminobenzonitrile, lemon yellow crystals, melting point 211-214° C., yield 63%
Compound B, from 2-amino-4-methylbenzonitrile, white powder, melting point 234-237° C., yield 67%
Compound C, from 4-aminobenzonitrile, lemon yellow crystals, melting point 157-160° C., yield 89%

EXAMPLE 3

Compound D was incorporated in epoxy resin formulations as follows.
Five formulation were prepared. Formulation I and Formulation IV are comparative formulations, representative of those used for the manufacture of matrix materials for aerospace composites and prepared without the use of Compound D. Formulations II, II and V are formulations utilising Compound D. Liquid epoxy resins (tetraglycidyl derivative of diphenylmethane diamine, MY721; triglycidyl derivative of p-aminophenol, MY0510, triglycidyl derivative of m-aminophenol, MY0600; all ex Huntsman) were blended with thermoplastic toughening agents (Polyethersulfone 5003P, PES, ex Sumitomo or Polyetherimide, Ultem 1000 ex GE Plastics) and aromatic amine curing agents (3,3'-diaminodiphenylsulfone, 3,3'-DDS and 4,43'-diaminodiphenylsulfone, 4,4'-DDS). The table summarises the formulation quantities as weight percentages. The blended resins were poured into moulds, degassed under vacuum and cured at 180° C. for 2 hours to produce rigid plaques for testing.
Mechanical testing in three point bending mode was carried out on a Mettler DMA/SDTA861 dynamic mechanical thermal analyser. Table 1 summarises the glass transition temperature (Tg) and flexural modulus of the cured resins.

TABLE 1

|  | I | II | III | IV | V |
|---|---|---|---|---|---|
| MY721 | 30.45 | 30.31 | 10.35 | 30.45 | 30.67 |
| MY0510 | 30.45 | 0 | 0 | 30.45 | 0 |
| MY0600 | 0 | 30.31 | 49.82 | 0 | 30.67 |
| 3,3'-DDS | 26.2 | 20.57 | 20.88 | 26.2 | 14.33 |
| 4,4'-DDS | 2.91 | 0 | 0 | 2.91 | 0 |
| Compound D | 0 | 8.81 | 8.94 | 0 | 14.33 |
| PES | 10 | 10 | 10 | 0 | 0 |
| Ultem | 0 | 0 | 0 | 10 | 10 |
| Tg, ° C. | 196 | 180 | 177 | 199 | 161 |
| Modulus, MPa | 2705 | 3503 | 3810 | 2922 | 3595 |

Table 1 shows that epoxy resins containing Compound D have significantly higher flexural moduli than those cured with other curing agents normally used in aerospace type epoxy resins.

The invention claimed is:
1. A curable epoxy resin comprising a compound having the formula

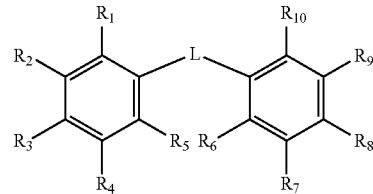

wherein L is a linking group, at least one of $R_1$ to $R_{10}$ comprising the group C≡N, at least one of $R_1$ to $R_5$ and at least one of $R_6$ to $R_{10}$ comprise the group $NH_2$.

2. A composite material comprising an epoxy resin according to claim 1, which has been cured.

3. A process for the preparation of a compound having the formula

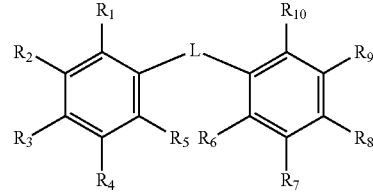

wherein L is a linking group, at least one of $R_1$ to $R_{10}$ comprises the group C≡N, at least one of $R_1$ to $R_5$ and at least one of $R_6$ to $R_{10}$ comprise the group $NH_2$, comprising the steps of bringing together starting material comprising

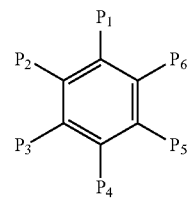

wherein at least one of $P_1$ to $P_6$ comprises C≡N and at least one of $P_1$ to $P_6$ comprises $NH_2$ into intimate contact with a kaolin clay and an aldehyde.

4. The curable epoxy resin, composite material or process for the preparation of the compound according to claim 1, 2 or 3, wherein L is selected from $CH_2$, $SO_2$, O or $CHCH_3$.

5. The curable epoxy resin, composite material or process for the preparation of the compound according to claim 4 wherein L is $CH_2$.

6. The curable epoxy resin, composite material or process for the preparation of the compound according to claim 1, 2 or 3, comprising at least two C≡N groups.

7. The curable epoxy resin, composite material or process for the preparation of the compound according to claim 6, wherein a C≡N group is on each benzene ring.

8. The curable epoxy resin, composite material or process for the preparation of the compound according to claim 1, 2 or 3, wherein $R_1$=$R_{10}$, $R_2$=$R_9$, $R_3$=$R_8$, $R_4$=$R_7$ and $R_5$=$R_6$.

9. The curable epoxy resin, composite material or process for the preparation of the compound according to claim 1, 2 or 3, wherein each of the remaining $R_1$ to $R_{10}$ comprise H or $C_1$ to $C_5$ alkyl.

10. The curable epoxy resin, composite material or process for the preparation of the compound according to claim 1, 2 or 3, wherein any C═N group and $NH_2$ group are attached to carbons in a benzene ring which are not adjacent to each other.

11. A process according to claim 3, wherein the kaolin clay is kaolinite.

12. A process according to claim 3, wherein the aldehyde is methanal.

13. A process according to claim 3, wherein each of the remaining $P_1$ to $P_6$ comprise H or $C_1$ to $C_5$ alkyl.

14. A process according to claim 3, wherein the C═N and $NH_2$ groups in the starting material are attached to carbons in the benzene ring which are not adjacent to each other.

* * * * *